(12) United States Patent
Williams

(10) Patent No.: US 9,668,740 B2
(45) Date of Patent: Jun. 6, 2017

(54) ANVIL ASSEMBLY WITH SLIDING SLEEVE

(71) Applicant: Covidien LP, Mansfield, MA (US)

(72) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 556 days.

(21) Appl. No.: 13/917,729

(22) Filed: Jun. 14, 2013

(65) Prior Publication Data

US 2014/0367444 A1    Dec. 18, 2014

(51) Int. Cl.
*A61B 17/11* (2006.01)
*A61B 17/04* (2006.01)
*A61B 17/115* (2006.01)
*A61B 17/072* (2006.01)

(52) U.S. Cl.
CPC . *A61B 17/1155* (2013.01); *A61B 2017/07257* (2013.01)

(58) Field of Classification Search
CPC ....................................... A61B 17/115
USPC ....................................... 227/175.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |

(Continued)

FOREIGN PATENT DOCUMENTS

| | | |
|---|---|---|
| CA | 908529 | 8/1972 |
| DE | 1057729 B | 5/1959 |

(Continued)

OTHER PUBLICATIONS

European Search Report 14172389.0-1654 dated Nov. 24, 2014.

*Primary Examiner* — Andrew M Tecco
*Assistant Examiner* — Praachi M Pathak

(57) ABSTRACT

An anvil assembly having a sliding sleeve is provided. The anvil assembly includes an anvil center rod assembly, a head assembly pivotally secured to the anvil center rod assembly, and a sleeve member slidably disposed about the anvil center rod assembly. The sleeve member is configured to slide relative to the anvil center rod assembly as the head assembly pivots relative to the anvil center rod assembly.

13 Claims, 10 Drawing Sheets

(56) References Cited

U.S. PATENT DOCUMENTS

| | | |
|---|---|---|
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,381,943 A * | 1/1995 | Allen .............. A61B 17/0682 227/177.1 |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |

(56) References Cited

U.S. PATENT DOCUMENTS

| | | |
|---|---|---|
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 * | 10/2008 | Milliman ............ A61B 17/068 227/178.1 |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |

(56) References Cited

U.S. PATENT DOCUMENTS

| | | | |
|---|---|---|---|
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky et al. | |
| 8,109,426 B2 | 2/2012 | Milliman et al. | |
| 9,010,605 B2 * | 4/2015 | Olson | A61B 17/1155 227/175.1 |
| 2003/0111507 A1 | 6/2003 | Nunez | |
| 2004/0195289 A1 * | 10/2004 | Aranyi | A61B 17/072 227/180.1 |
| 2005/0051597 A1 | 3/2005 | Toledano | |
| 2005/0107813 A1 | 5/2005 | Gilete Garcia | |
| 2005/0125009 A1 | 6/2005 | Perry et al. | |
| 2005/0145674 A1 | 7/2005 | Sonnenschein et al. | |
| 2005/0145675 A1 | 7/2005 | Hartwick et al. | |
| 2005/0205639 A1 * | 9/2005 | Milliman | A61B 17/115 227/175.1 |
| 2006/0000869 A1 | 1/2006 | Fontayne | |
| 2006/0011698 A1 | 1/2006 | Okada et al. | |
| 2006/0047307 A1 | 3/2006 | Ortiz et al. | |
| 2006/0144897 A1 | 7/2006 | Jankowski et al. | |
| 2006/0201989 A1 | 9/2006 | Ojeda | |
| 2006/0241692 A1 | 10/2006 | McGuckin, Jr. et al. | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2008/0230581 A1 * | 9/2008 | Marczyk | A61B 17/115 227/176.1 |
| 2009/0230170 A1 | 9/2009 | Milliman | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2009/0255976 A1 | 10/2009 | Marczyk et al. | |
| 2009/0302089 A1 | 12/2009 | Harari et al. | |
| 2010/0001037 A1 | 1/2010 | Racenet et al. | |
| 2010/0019016 A1 | 1/2010 | Edoga et al. | |
| 2010/0038401 A1 * | 2/2010 | Milliman | A61B 17/1114 227/175.1 |
| 2010/0051668 A1 | 3/2010 | Milliman et al. | |
| 2010/0065607 A1 | 3/2010 | Orban, III et al. | |
| 2010/0084453 A1 | 4/2010 | Hu | |
| 2010/0089971 A1 | 4/2010 | Milliman et al. | |
| 2010/0108739 A1 | 5/2010 | Holsten et al. | |
| 2010/0108740 A1 | 5/2010 | Pastorelli et al. | |
| 2010/0108741 A1 | 5/2010 | Hessler et al. | |
| 2010/0133319 A1 | 6/2010 | Milliman et al. | |
| 2010/0147923 A1 | 6/2010 | D'Agostino et al. | |
| 2010/0163598 A1 | 7/2010 | Belzer | |
| 2010/0170932 A1 | 7/2010 | Wenchell et al. | |
| 2010/0224668 A1 | 9/2010 | Fontayne et al. | |
| 2010/0230465 A1 | 9/2010 | Smith et al. | |
| 2010/0230466 A1 | 9/2010 | Criscuolo et al. | |
| 2010/0230467 A1 | 9/2010 | Criscuolo et al. | |
| 2010/0258611 A1 | 10/2010 | Smith et al. | |
| 2010/0264195 A1 | 10/2010 | Bettuchi | |
| 2010/0270356 A1 | 10/2010 | Holsten et al. | |
| 2010/0282815 A1 | 11/2010 | Bettuchi et al. | |
| 2010/0301098 A1 | 12/2010 | Kostrzewski | |
| 2010/0327041 A1 | 12/2010 | Milliman et al. | |
| 2011/0006100 A1 | 1/2011 | Milliam | |
| 2011/0006102 A1 | 1/2011 | Kostrzewski | |
| 2011/0011916 A1 | 1/2011 | Levine | |
| 2011/0017800 A1 | 1/2011 | Viola | |
| 2011/0024476 A1 | 2/2011 | Bettuchi et al. | |
| 2011/0024481 A1 | 2/2011 | Bettuchi et al. | |
| 2011/0036889 A1 | 2/2011 | Heinrich et al. | |
| 2011/0036894 A1 | 2/2011 | Bettuchi | |
| 2011/0042442 A1 | 2/2011 | Viola et al. | |
| 2011/0042443 A1 | 2/2011 | Milliman et al. | |
| 2011/0057016 A1 | 3/2011 | Bettuchi | |
| 2011/0089219 A1 | 4/2011 | Hessler | |
| 2011/0095067 A1 | 4/2011 | Ohdaira | |
| 2011/0095068 A1 | 4/2011 | Patel | |
| 2011/0095069 A1 | 4/2011 | Patel et al. | |
| 2011/0095070 A1 | 4/2011 | Patel et al. | |
| 2011/0101065 A1 | 5/2011 | Milliman | |
| 2011/0114697 A1 | 5/2011 | Baxter, III et al. | |
| 2011/0114698 A1 | 5/2011 | Baxter, III et al. | |
| 2011/0114699 A1 | 5/2011 | Baxter, III et al. | |
| 2011/0114700 A1 | 5/2011 | Baxter, III et al. | |
| 2011/0114701 A1 | 5/2011 | Hessler | |
| 2011/0118761 A1 | 5/2011 | Baxter, III et al. | |
| 2011/0130788 A1 | 6/2011 | Orban, III et al. | |
| 2011/0139852 A1 | 6/2011 | Zingman | |
| 2011/0139853 A1 | 6/2011 | Viola | |
| 2011/0144640 A1 | 6/2011 | Heinrich et al. | |
| 2011/0147432 A1 | 6/2011 | Heinrich et al. | |
| 2011/0147434 A1 | 6/2011 | Hueil et al. | |
| 2011/0147435 A1 | 6/2011 | Heinrich et al. | |
| 2011/0192882 A1 | 8/2011 | Hess et al. | |
| 2011/0210156 A1 | 9/2011 | Smith et al. | |
| 2011/0220703 A1 | 9/2011 | Orban, III | |
| 2011/0248067 A1 | 10/2011 | Takei | |
| 2013/0092720 A1 * | 4/2013 | Williams | A61B 17/1155 227/181.1 |
| 2013/0105544 A1 * | 5/2013 | Mozdzierz | A61B 17/1155 227/175.1 |
| 2013/0153631 A1 * | 6/2013 | Vasudevan | A61B 17/1155 227/175.2 |
| 2013/0181036 A1 * | 7/2013 | Olson | A61B 17/1155 227/180.1 |
| 2015/0129635 A1 * | 5/2015 | Williams | A61B 17/115 227/177.1 |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2586384 A1 | 5/2013 |
| EP | 2614784 A2 | 7/2013 |
| EP | 2682061 A2 | 1/2014 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | WO 8706448 A | 11/1987 |
| WO | WO 8900406 A1 | 1/1989 |
| WO | WO 9006085 A1 | 6/1990 |
| WO | WO 01/54594 A1 | 8/2001 |
| WO | WO 2008/107918 A1 | 9/2008 |

* cited by examiner

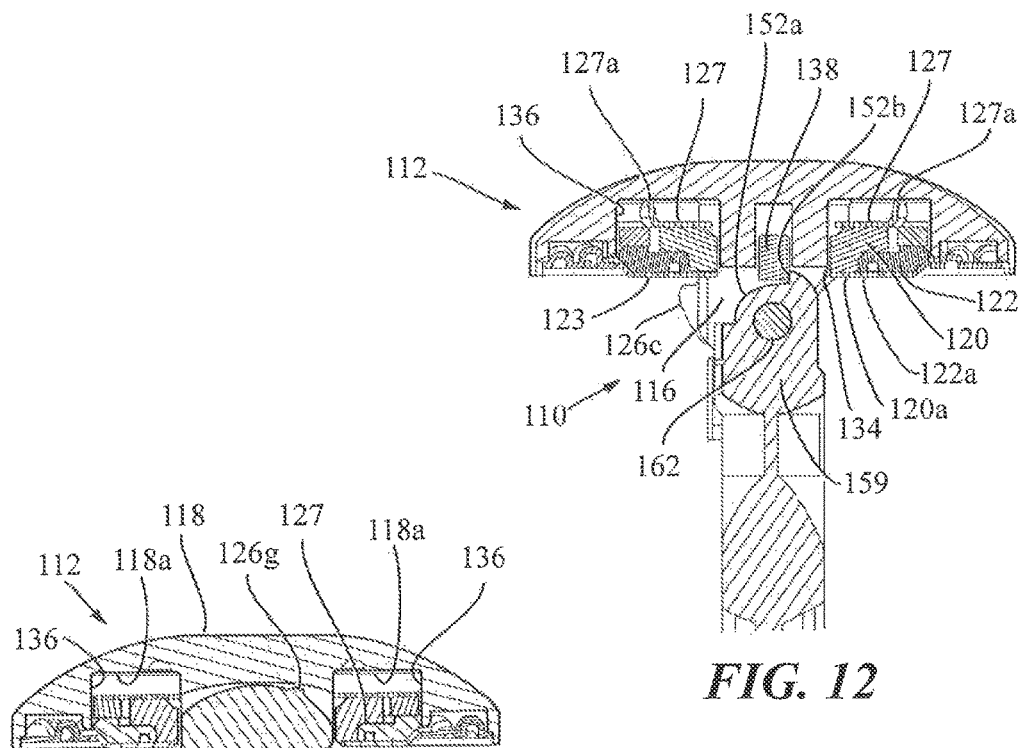
*FIG. 12*
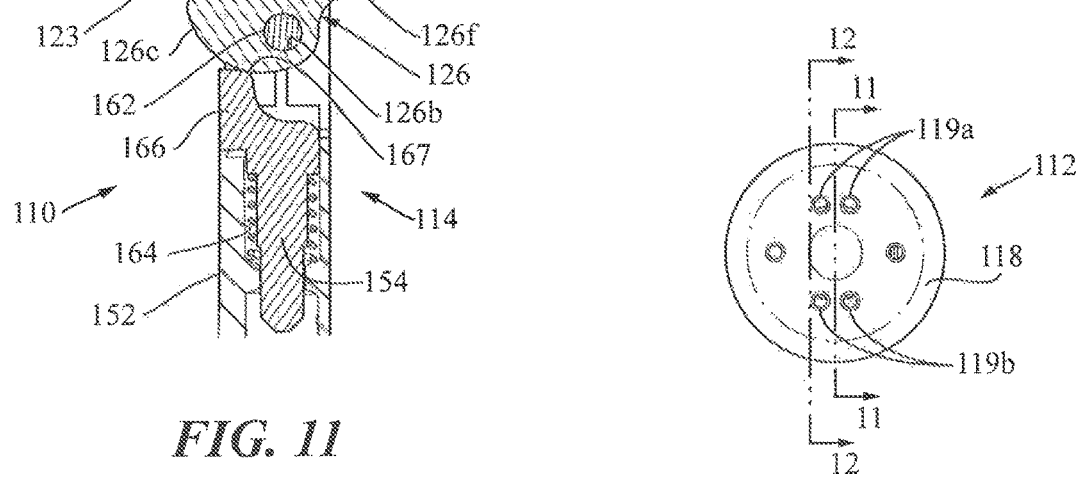
*FIG. 11*
*FIG. 10*

US 9,668,740 B2

ANVIL ASSEMBLY WITH SLIDING SLEEVE

BACKGROUND

Technical Field

The present disclosure relates generally to an anvil assembly which is suitable for use with a circular anastomosis stapler. More specifically, the present disclosure relates to an anvil assembly having a tiltable head with a sliding sleeve.

Background of Related Art

Circular anastomosis staplers which include an anvil assembly having a tiltable anvil head are known in the art. One such circular anastomosis stapler is disclosed in commonly owned U.S. Pat. No. 8,109,426 ("the '426 Patent") which is incorporated herein by reference in its entirety. The anvil assembly includes an anvil head pivotally secured on a distal end of a connection post of the anvil assembly. The anvil assembly is pivotable from a first tilted position to facilitate insertion of the anvil assembly trans-orally, to a non-tilted operative position wherein the anvil head is perpendicular to the connection post. Following the firing operation of the circular stapler and as the anvil head is separated from the cartridge assembly of the circular stapler, the anvil head continues to pivot about the distal end of the connection post to a second tilted position, thereby reducing the profile of the anvil head to permit removal of the anvil assembly through the newly created anastomosis ring. The anvil assembly is spring loaded to tilt to a maximum angle allowed by the circular stapler and/or anvil head geometry. Tilting the anvil head to its maximum angle facilitates pulling the anvil head through the anastomosis ring and removing the anvil assembly from within the patient.

In certain instances, an anastomosis donut, i.e., the tissue severed by an annular knife of the stapling assembly during the anastomosis procedure, may become pinched by the anvil head as the anvil head is pivoted. When pinching of the anastomosis donut occurs, the anvil head is inhibited from tilting to its maximum angle. As a result, the anvil head may require a greater force to withdraw the anvil head through the anastomosis ring, thereby causing undesirable and unnecessary trauma to the anastomosis ring and/or.

Therefore, it would be beneficial to have an anvil assembly that prevents pinching of tissue or another obstruction by the tiltable anvil head, and, thus, allow complete tilting of the anvil head.

SUMMARY

Accordingly, an anvil assembly having a sliding sleeve is provided. The anvil assembly includes an anvil center rod assembly, a head assembly pivotally secured to the anvil center rod assembly, and a sleeve member slidably disposed about the anvil center rod assembly. The sleeve member is configured to slide relative to the anvil center rod assembly as the head assembly pivots relative to the anvil center rod assembly.

In one embodiment, the sleeve member includes a sleeve body disposed about the anvil center rod assembly. The sleeve body may include a plurality of teeth for engaging the head assembly. The head assembly may include a housing and a post extending proximally from the housing. The post may include a plurality of teeth configured to engage the plurality of teeth formed on the sleeve body as the head assembly pivots relative to the anvil center rod assembly.

In some embodiments, the head assembly is configured to pivot between a first tilted position, a non-tilted operated position, and a second tilted position. Pivoting of the anvil assembly from the non-tilted position to the second tilted position may cause the sleeve body to move proximally relative to anvil center rod assembly. Pivoting of the anvil assembly from the non-tilted position to the first tilted position may cause the sleeve body to move distally relative to anvil center rod assembly. The head assembly may be, for example, tilted seventy degrees (70°) relative to the anvil center rod assembly when the head assembly is in the first tilted position. The head assembly may be perpendicular to the anvil center rod when the head assembly is in the non-tilted operative position. The head assembly may be tilted seventy degrees (70°) relative to the anvil center rod assembly when the head assembly is in the second tilted position. In one embodiment, the head assembly moves through one hundred-forty degrees (140°) when the head assembly tilts from the first tilted position, through the non-tilted position, to the second tilted position.

Also provided is a surgical stapler having an anvil assembly with a sleeve member. The surgical stapler includes a handle assembly, an elongated body portion extending distally from the handle assembly, a shell assembly secured to a distal end of the elongated body portion, and an anvil assembly selectively secured relative to the shell assembly. The anvil assembly includes an anvil center rod assembly, a head assembly pivotally secured to the anvil center rod assembly, and a sleeve member slidably disposed about the anvil center rod assembly. The sleeve member is slidable relative to the anvil center rod assembly as the head assembly pivots relative to the anvil center rod assembly.

In the embodiments, the sleeve member is disposed between the shell assembly and the head assembly during firing of the surgical stapler to receive an anastomosis donut. The sleeve member may be configured to move proximally as the head assembly is moved away from the shell assembly subsequent to firing of the surgical stapler.

BRIEF DESCRIPTION OF THE DRAWINGS

Various embodiments of the presently disclosed tilt anvil assembly are disclosed herein with reference to the drawings wherein:

FIG. 10 is an end view of the anvil assembly shown in FIGS. 2 and 3, in the operable position;

FIG. 11 is an enlarged cross-sectional view taken along line 11-11 shown in FIG. 10, with sleeve assembly removed;

FIG. 12 is an enlarged cross-sectional view taken along line 12-12 shown in FIG. 10, with sleeve assembly removed;

DETAILED DESCRIPTION OF EMBODIMENTS

Figure 1:
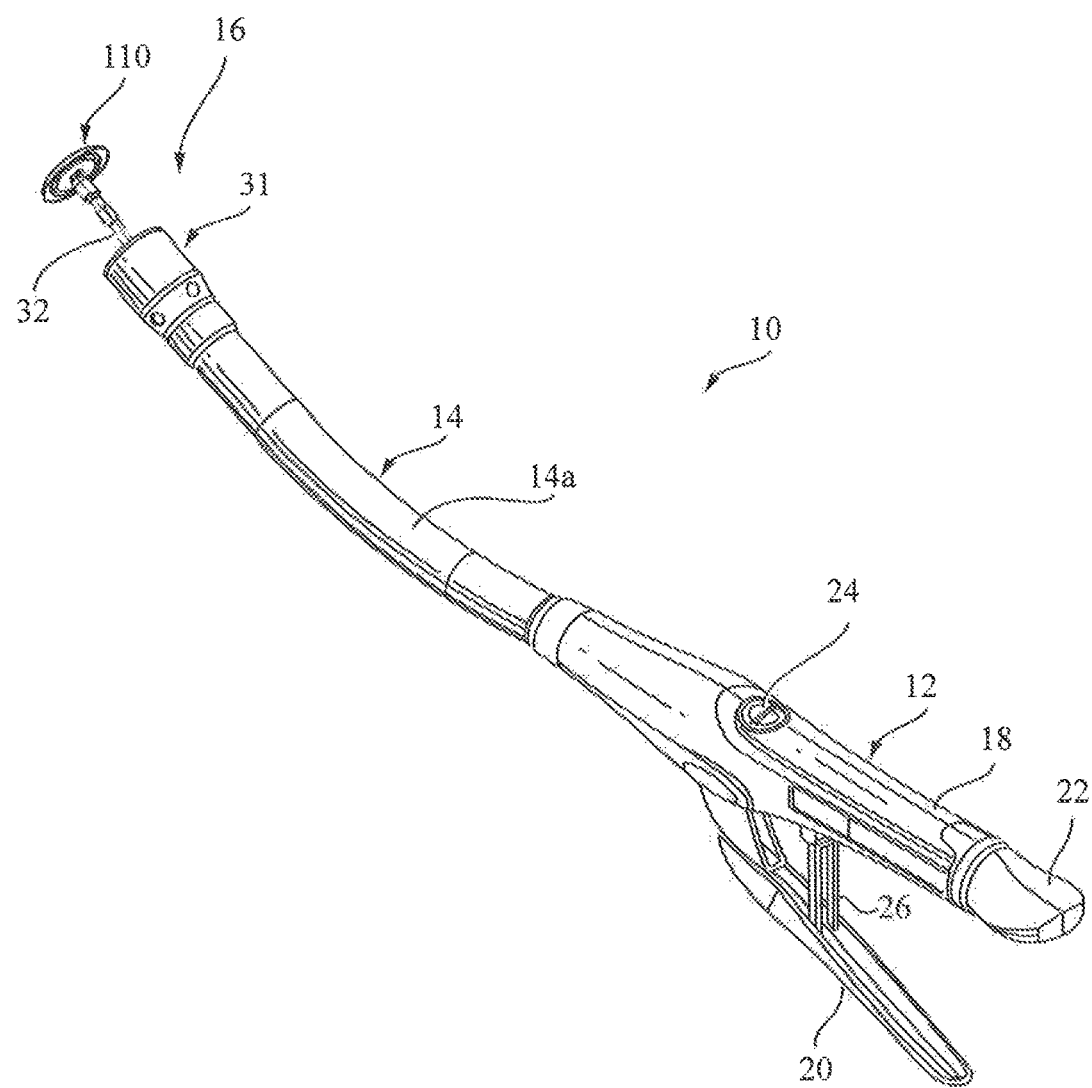
FIG. 1 is a side perspective view of a surgical stapling device including an anvil assembly according to an embodiment of the present disclosure.

Embodiments of the presently disclosed anvil assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

FIGS. 1-16 illustrate an anvil assembly 110 for use with a surgical stapling device 10 (FIG. 1) suitable for performing, for example, circular anastomoses of hollow tissue organs and hemorrhoid surgeries. Although shown as relates to anvil assembly 110 for use with surgical stapling device 10, it is envisioned that the aspects of the present disclosure may be modified for use with any anvil assembly having an anvil head capable of being pivoted from a first tilted position, through a non-tilted operable position, to a second tilted position. It is further envisioned that the aspects of the present disclosure may also be modified for use with an anvil assembly in which the anvil head is not capable of pivoting to a first tilted position and is instead provided to a clinician in the non-tilted operable position.

FIG. 1 illustrates an embodiment of a surgical stapling device configured for use with a tilt anvil assembly according to the present disclosure. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of body portion 14 and distal head portion 16 may also be varied to suit a particular surgical procedure.

With reference still to FIG. 1, handle assembly 12 includes a stationary handle 18, a firing trigger 20, a rotatable approximation knob 22, and an indicator 24. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 110 and a shell assembly 31. A more detailed discussion of surgical stapler 10 is disclosed in commonly owned U.S. Pat. Nos. 7,364, 060 and 7,303,106 ("the '060 Patent" and "the '106 Patent"), the contents of which are incorporated herein by reference in their entirety.

In any of the embodiments disclosed herein, the stapling apparatus 10 can include the manually actuated handle assembly of FIG. 1 and as described above, or can include a powered actuator assembly having drive members. For example, U.S. patent application Ser. No. 12/946,082, filed Nov. 15, 2010, the entire disclosure of which is hereby incorporated by reference herein, discloses a surgical device having a powered actuator assembly. Such actuator assembly can be powered by a motorized handle. The handle may include a power source, such as one or more batteries, or may be configured to be attached to a power source, such as a transformer, generator, or electrical outlet. It is also contemplated that, in any of the embodiments disclosed herein, the apparatus has a replaceable head or replaceable loading unit which includes the cartridge assembly, anvil member and associated mechanisms. In those embodiments, the entire distal end of the instrument is removable and replaceable. It is also contemplated that, in any of the embodiments disclosed herein, the instrument can be disposable, re-sterilizable and reusable, or certain portions of the instrument can be re-sterilizable and reusable (e.g., reposable).

Figure 2:
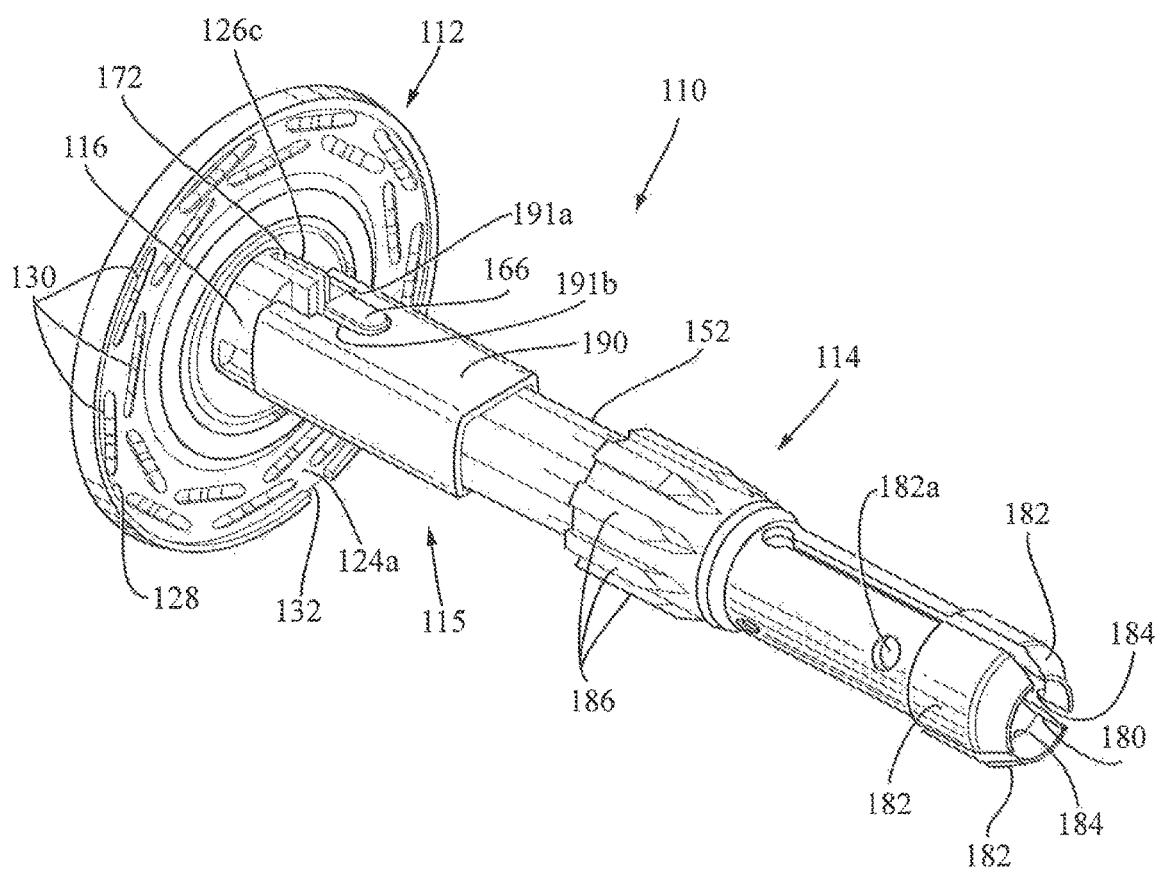
FIG. 2 is a side perspective view of the anvil assembly shown in FIG. 1, in a second or operable position.
Figure 3:
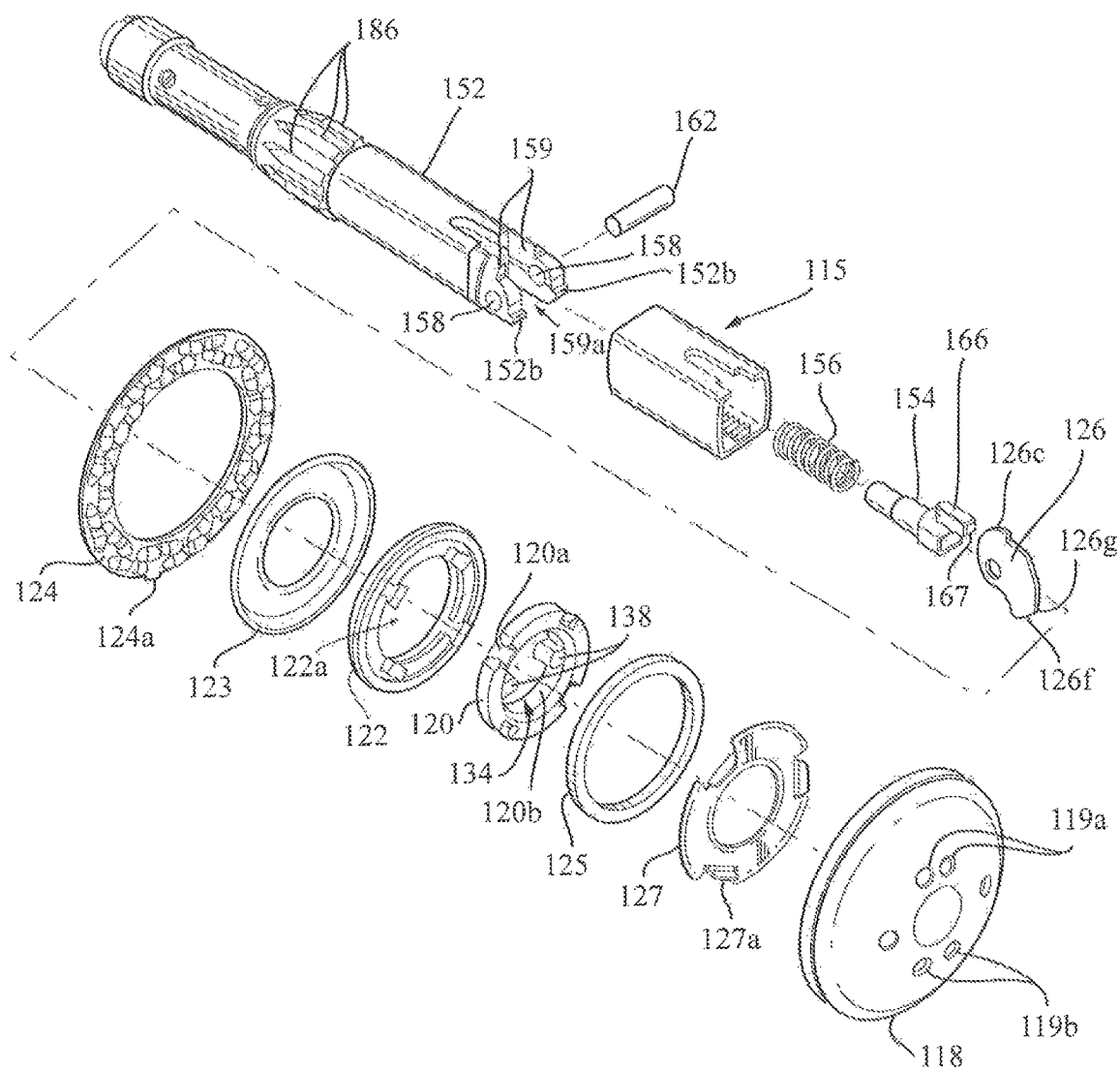
FIG. 3 is an exploded prospective view of the anvil assembly shown in FIG. 2.

Referring now to FIGS. 2-9, an embodiment of the anvil assembly of the present disclosure is shown generally as reference numeral 110. Referring initially to FIGS. 2-5, anvil assembly 110 is shown in a non-tilted or operative position wherein the staple deforming pockets 130 face the staple slots (not shown) of surgical stapler 10 (FIG. 1). Anvil assembly 110 includes a head assembly 112, a center rod assembly 114, and a sleeve member 115. Head assembly 112 includes a post 116, a housing 118, a backup member or plate 120 (FIG. 3), a cutting ring 122 (FIG. 3), a cutting ring cover 123 (FIG. 3), an anvil plate 124, a spacer or washer 125 (FIG. 3), a cam latch member 126 (FIG. 5), and a retainer member 127 (FIG. 3).

Figure 4:
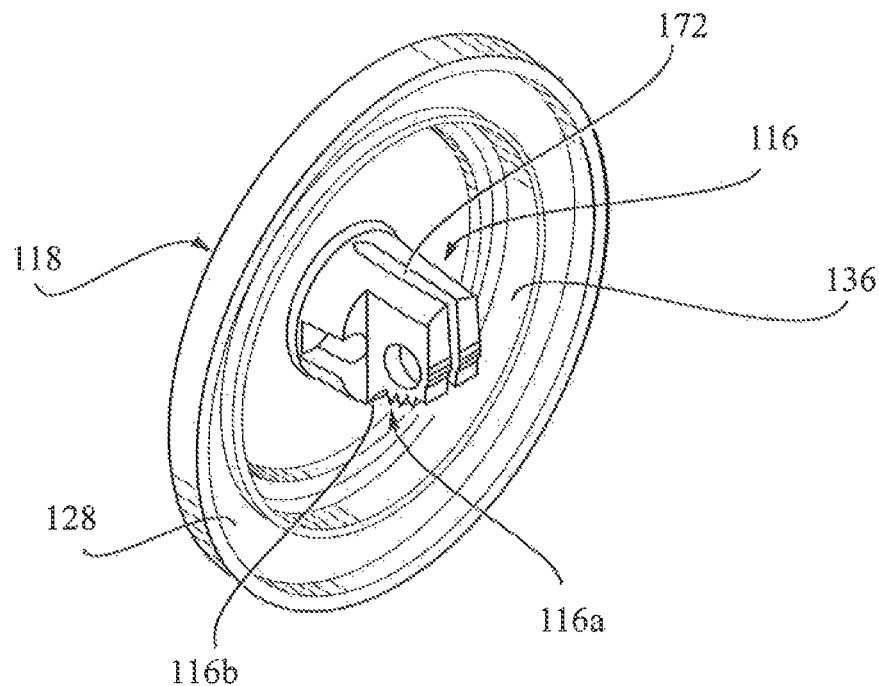
FIG. 4 is bottom perspective view of the housing of the anvil head assembly of the anvil assembly shown in FIGS. 2 and 3.
Figure 16:
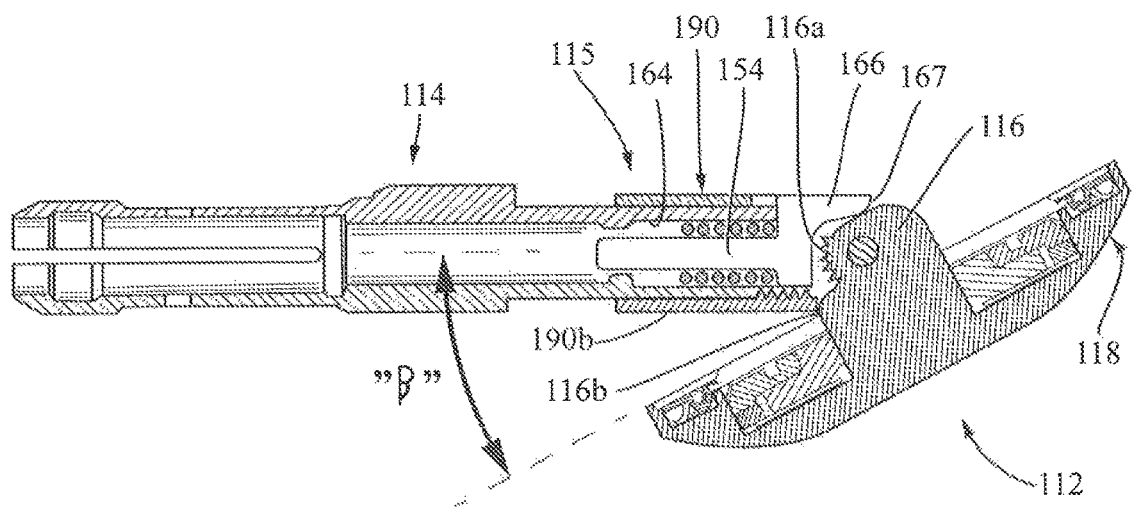

With reference to FIG. 4, post 116 is monolithically formed with and centrally positioned within housing 118. Alternately, housing 118 and post 116 may be formed separately and fastened together using a known fastening technique, e.g., welding. A plurality of teeth 116a are formed on a proximal end of post 116. As will be described in greater detail below, teeth 116a are configured to selectively engage sleeve member 115 during operation of head assembly 112. As will also be described in greater detail below, an outward facing surface 116b of post 116 is configured to engage sleeve member 115 during movement of anvil head assembly 112 from the non-tilted operational position (FIG. 14) to the second tilted position (FIG. 16).

Figure 7:
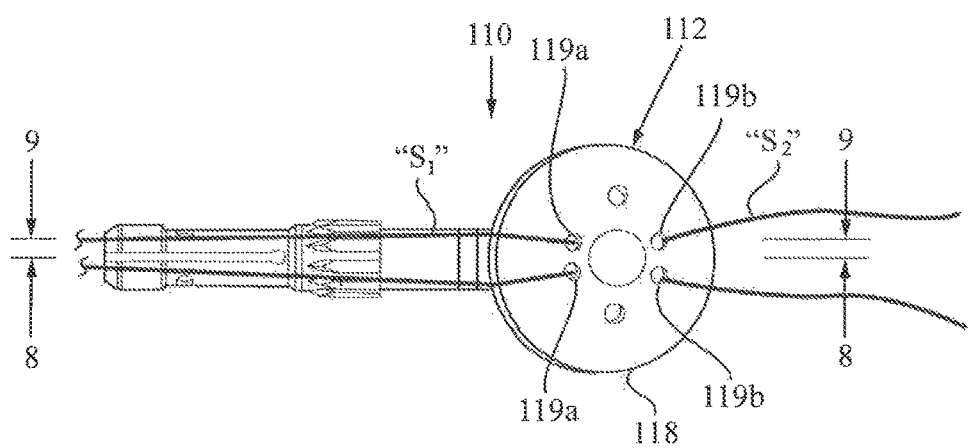
FIG. 7 is a top view of the anvil assembly shown in FIGS. 2 and 3, in the first position and including a pair of sutures received through the head assembly.
Figure 8:
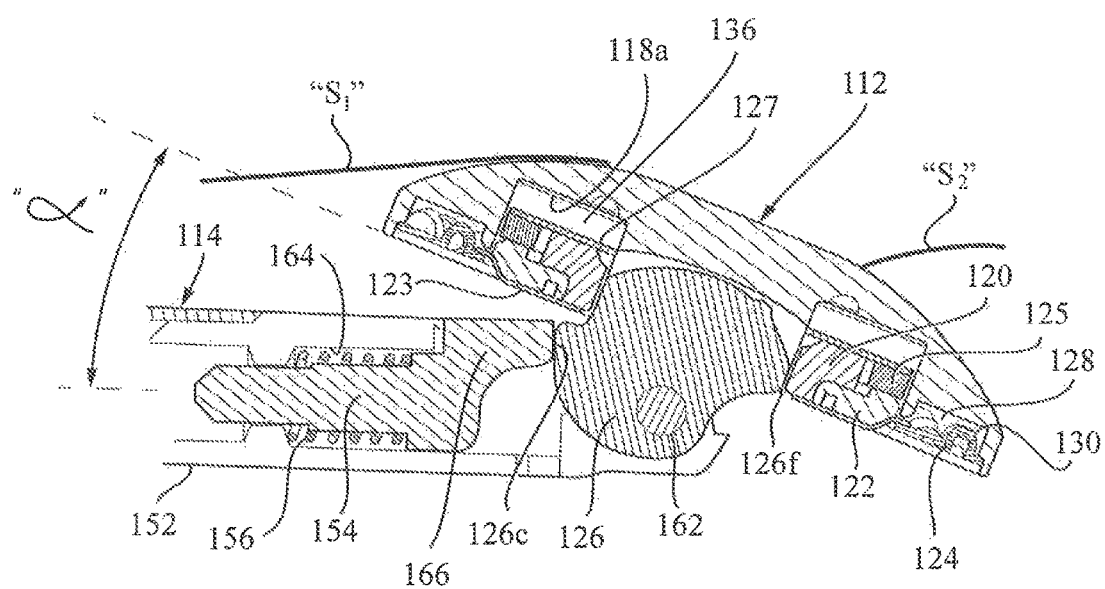
FIG. 8 is an enlarged cross-sectional view taken along line 8-8 shown in FIG. 7.
Figure 9:
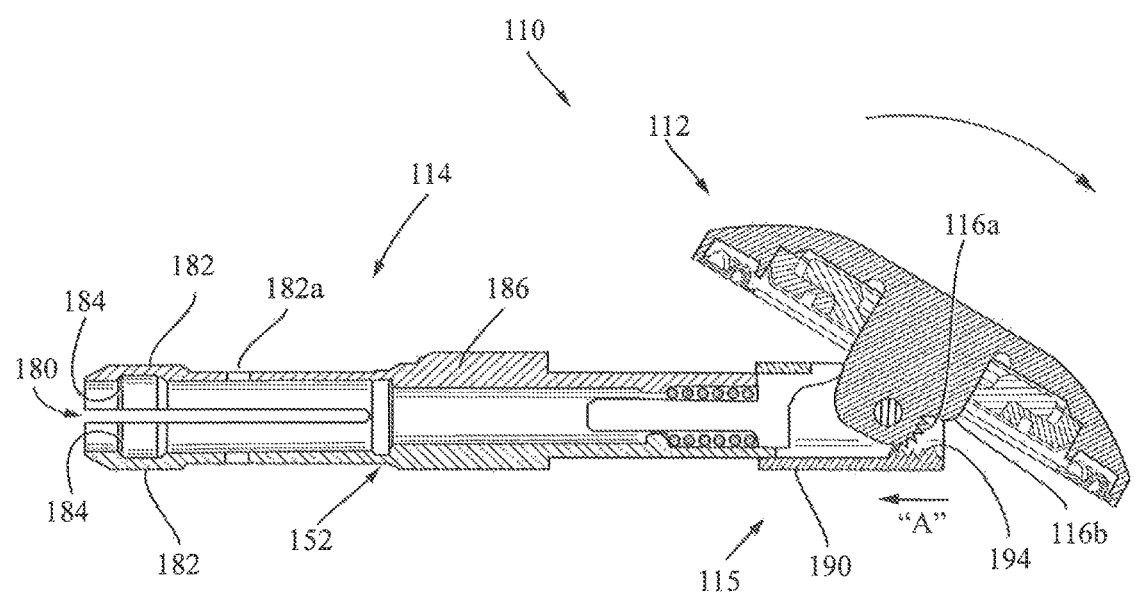
FIG. 9 is a cross-sectional view taken along line 9-9 shown in FIG. 7.
Figure 13:
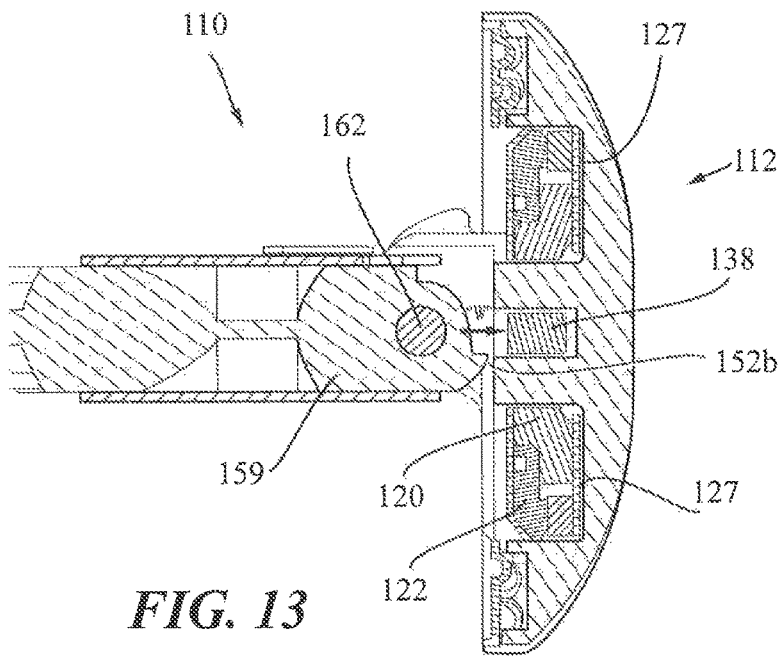
FIG. 13 is a cross-sectional view of the anvil assembly shown in FIGS. 2 and 3 subsequent to firing of the surgical stapling device shown in FIG. 1.

With particular reference now to FIG. 7, housing 118 includes openings 119a, 119b sized and dimensioned to receive one or more sutures "S". During use, a first suture "$S_1$" is inserted through openings 119a and is used to retain head assembly 112 in the first tilted position (as shown in FIGS. 8 and 9) during insertion of anvil assembly 110 within a patient. More particularly, first suture "$S_1$" operates as a tensioning member to maintain the head assembly in the first tilted position. A second suture "$S_2$" is inserted through openings 119b and is configured to permit retrieval of tilt anvil assembly 110 from within a patient if desired. During trans-oral insertion of anvil assembly 110, second suture "$S_2$" extends from the mouth of patient, permitting the anvil assembly 110 to be retrieved trans-orally. As shown, second suture "$S_2$" extends in a direction opposite the direction of suture "$S_1$".

With reference back to FIGS. 2 and 3, anvil plate 124 is supported in an outer annular recess 128 of housing 118 and includes a plurality of staple deforming pockets 130 for receiving and deforming staples. At least one tab 124a extends radially outwardly from anvil plate 124 and is received within a cutout 132 (FIG. 2) formed in an outer rim of housing 118. Tab 124a and cutout 132 function to align or properly position anvil plate 124 within annular recess 128 of housing 118.

With particular reference to FIGS. 2-4 and 8, head assembly 112 will be described in detail. Backup plate 120 includes a central opening 134 which is positioned about post 116 within an inner annular recess 136 of housing 118 between post 116 and outer annular recess 128. Backup plate 120 includes a raised platform 120a. Cutting ring 122 includes an opening 122a having a configuration substantially the same as platform 120a. Cutting ring cover 123 is secured to an outwardly facing or proximal surface of cutting ring 122 using, for example, an adhesive. Alternately, cutting ring 122 need not have a cover. Cutting ring 122 and backup plate 120 are slidably mounted about post 116. Backup plate 120 includes a pair of inwardly extending fingers 138 which will be described in further detail below.

With reference still to FIGS. 2-4 and 8, retainer member 127 is positioned in inner annular recess 136 between backup plate 120 and a back wall 118a of housing 118. In one embodiment, and as shown, retainer member 127 is annular and includes a plurality of deformable tabs 127a which engage a rear surface of backup plate 120. Retainer member 127 prevents backup plate 120 and cutting ring 122 from moving or being pushed into inner annular recess 136 of housing 118 until a predetermined force sufficient to deform tabs 127a has been applied to the backup plate/cutting ring assembly. The predetermined force can be close to, but is less than, the force applied by an annular cutting blade of a surgical stapling device when it engages, for example, the cutting ring of anvil assembly 110. When the predetermined force is reached, e.g., during cutting of tissue, backup plate 120 is urged into inner annular recess 136 and compresses retainer member 127. It is envisioned that other crushable, deformable, collapsible or movement restricting members may be used to retain the backup plate/cutting ring assembly in a fixed position until a predetermined force has been applied to the backup plate/cutting ring assembly.

As illustrated in FIGS. 2, 3, and 8, anvil center rod assembly 114 includes a center rod 152, a plunger 154, and plunger spring 156. A first end of center rod 152 includes a pair of arms 159 which defines a cavity 159a. Each arm 159 has a transverse throughbore 158 which is aligned with a central longitudinal axis of center rod 152. Post 116 of anvil head assembly 112 is dimensioned to be positioned within cavity 159a and also includes a transverse throughbore (not shown). A pivot member 162 pivotally secures post 116 to center rod 152 via the throughbores such that anvil head assembly 112 may be pivotally mounted to anvil center rod assembly 114.

Figure 5:
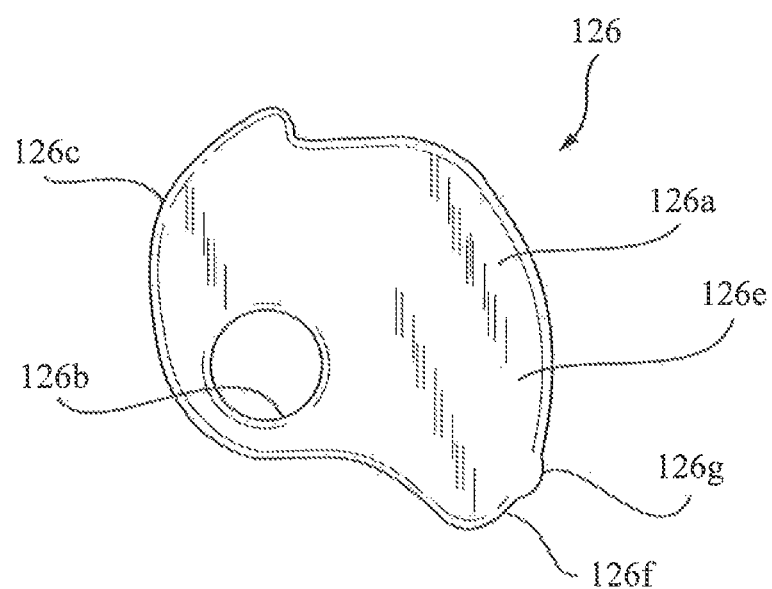
FIG. 5 is a side view of a cam latch member of the anvil assembly shown in FIGS. 2 and 3.
Figure 6A:
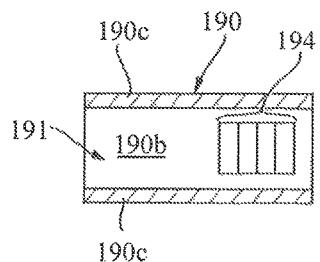
FIG. 6A is a cross-sectional view taken along line 6A-6A shown in FIG. 6.
Figure 6D:
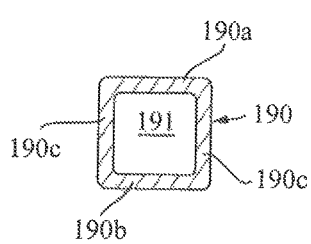
FIG. 6D is a cross-sectional view taken along line 6D-6D shown in FIG. 6.
Figure 6:
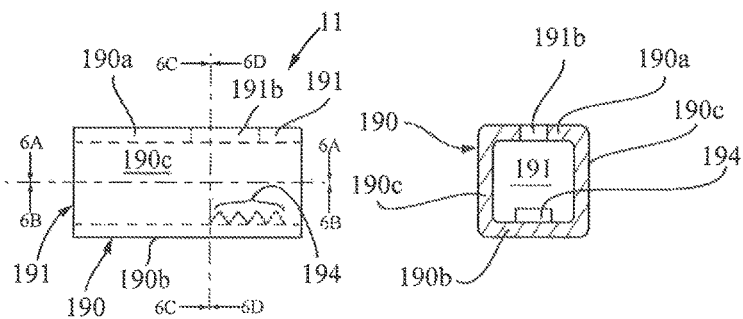
FIG. 6 is a side view of the sleeve body of the sleeve assembly of the anvil assembly shown in FIGS. 2 and 3.
Figure 6C:
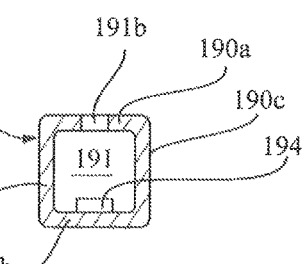
FIG. 6C is a cross-sectional view taken along line 6C-6C shown in FIG. 6.
Figure 6B:
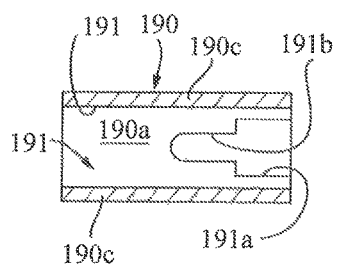
FIG. 6B is a cross-sectional view taken along line 6B-6B shown in FIG. 6.

Turning briefly to FIG. 5, cam latch member 126 includes a body 126a having a throughbore 126b. Throughbore 126b is dimensioned to receive pivot member 162 (FIG. 3) such that cam latch member 126 is pivotally mounted within transverse slot 172 (FIG. 2) of post 116 about pivot member 162.

Referring now to FIGS. 3, 5, and 8, cam latch member 126 includes a first body portion 126c which extends partially from slot 172 (FIG. 2) of post 116 and is positioned to be engaged by a finger 166 of plunger 154. First body portion 126c is configured such that the distance between the surface of first body portion 126c and throughbore 126b increase in a clockwise direction about cam latch member 126. In this manner, plunger 154 is able to move forward as cam latch member 126 rotates in a clockwise direction. Additionally, this configuration of first body portion 126c permits plunger 154 to be retracted as cam latch member 126 rotates in a counter-clockwise direction. Cam latch member 126 also includes an edge 126f, including a tab 126g. A leading portion of edge 126f is configured to be urged into engagement with an inner periphery 120b of backup plate 120 by an engagement finger 166 of plunger 154 when anvil head 112 is in the non-tilted operative position (FIG. 11). Tab 126g is configured to engage backwall 118a of housing 118 to prevent cam latch member 126 from rotating counter-clockwise relative to housing 118. Tab 126g prevents the cam for over rotation once the cut ring backup plate 120 is depressed. The tab 126g contacts with the bore of 120b to prevent over rotation.

With reference to FIGS. 3 and 8, plunger 154 is slidably positioned in a bore 164 formed in the first end of center rod 152. Plunger 154 includes an engagement finger 166 which is offset a radial distance from the pivot axis of anvil head assembly 112 and is biased into engagement with edge 126c of cam latch 126. Engagement of finger 166 with edge 126c of cam latch 126 presses a leading portion of edge 126f against an inner periphery of back plate 120 to urge anvil head assembly 112 to the non-tilted operative position on center rod 152.

With reference to FIGS. 2 and 9, a second end of center rod 152 includes a bore 180 defined by a plurality of flexible arms 182. Flexible arms 182 each include an opening 182a dimensioned to receive a projection formed on or connected to a shell assembly 31 (FIG. 1). The proximal ends of each of the flexible arms 182 include an internal shoulder 184 dimensioned to releasably engage shell assembly 31 of surgical stapling device 10 to secure anvil assembly 110 to the surgical stapling device. A plurality of splines 186 are formed about center rod 152. Splines 186 function to align anvil assembly 110 with the staple holding portion of a surgical stapling device.

With reference now to FIGS. 2, 3, and 6-6D, sleeve member 115 includes a sleeve body 190. Sleeve body 190 forms a substantially tubular member having top and bottom walls 190a, 190b, and a pair of sidewalls 190c. Sleeve body 190 defines a throughbore 191 configured to be slidingly received about a distal end of center rod 152. Top wall 190a defines a notch 191a and a slot 191b in a distal end of sleeve body 190. As seen in FIG. 2, notch 191a is configured to permit receipt of sleeve body 190 about post 116 of head assembly 112. As also seen in FIG. 2, slot 191b is configured to accommodate finger 166 of plunger 154 when sleeve member 115 is in a distal-most position. Sleeve body 190 includes a plurality of teeth 194 formed on the distal end of bottom wall 190b and extending into throughbore 191. As will be described in further detail below, teeth 194 of sleeve body 190 are configured to engage teeth 116a formed on post 116 of head assembly 112 to cause sliding movement of sleeve body 190 from a first, distal-most position (FIG. 9), through a second, operable position (FIG. 14) to a third, proximal-most position (FIG. 16). Sleeve body 190 may optionally include an annular flange (not shown) on the outer surface of either or both of the first and second ends to facilitate retention of the anastomosis donut (not shown) about sleeve body 190 as sleeve body 190 moves during a procedure.

With reference to FIG. 8, anvil head assembly 112 may be tilted "α" degrees relative to anvil center rod assembly 114 to the first tilted position by first suture "S₁". Titling of anvil head assembly 112 relative to anvil center rod assembly 114 by first suture "S₁" causes cam latch member 126 positioned within the inner periphery of the backup plate 120 to rotate, causing body portion 126c of cam latch member 126 to engage finger 166 of plunger 154. As cam latch assembly 126 rotates counterclockwise (as viewed in FIG. 8) with the tilting of anvil head assembly 112, plunger 154 is retracted within bore 164 of anvil center rod assembly 114, thereby compressing spring 156. In this manner, finger 166 of plunger 154 is distally biased against body portion 126c of cam latch member 126. As can be appreciated with reference to FIGS. 9 and 14, as anvil head assembly 112 is pivoted from the non-tilted operative position (FIG. 14) to the first tilted position (FIG. 9), teeth 116a formed on post 116 of housing 118 engage teeth 194 formed on sleeve body 190 of sleeve member 115 causing sleeve body 190 to advance distally, in a direction opposite to that indicated by arrow "A" in FIG. 9.

Figure 14:
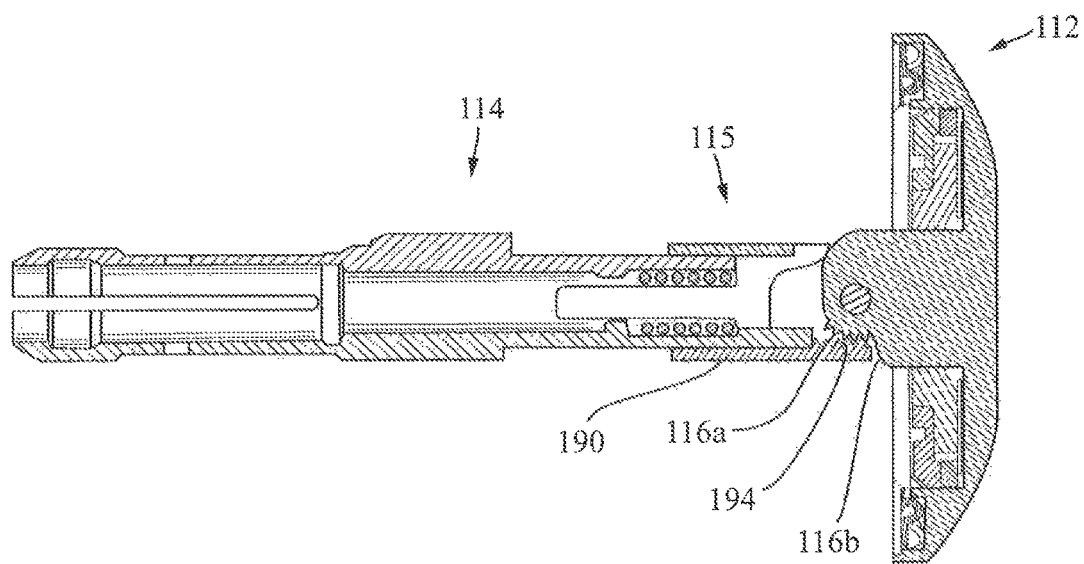
FIG. 14 is an alternative cross-sectional view of the anvil assembly as shown in FIG. 13.
Figure 15:
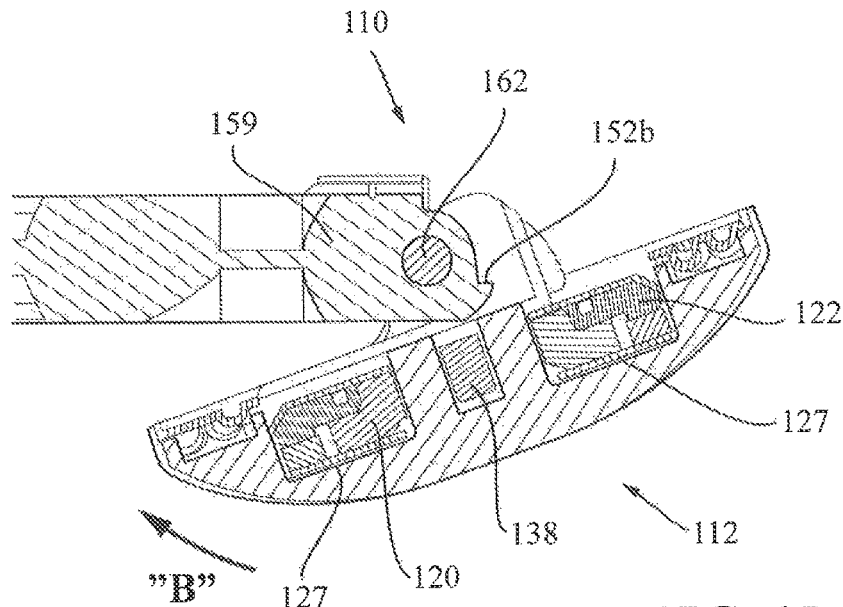
FIG. 15 is a cross-sectional view of the anvil assembly shown in FIGS. 2 and 3 in a second, tilted position; and, FIG. 16 is an alternative cross-sectional view of the anvil assembly as shown in FIG. 15.

With reference back to FIG. 8, severing of suture "S₁" permits plunger 154 to extend from within bore 164, thereby causing finger 166 to engage body portion 126c of cam latch member 126. Rotation of cam latch member 126 (clockwise as viewed in the orientation of FIG. 8) causes edge 126f of latch member 126, engaged with the inner periphery of backup plate 120, to urge anvil head assembly 112 to return to the non-tilted operative position (e.g. the position of FIG. 11). Additionally, the distal end of stapling device 10 (FIG. 1) may be configured to engage finger 166 of plunger 154 as anvil assembly 110 is attached to surgical stapling device 10. In this manner, the distal end of surgical stapling device 10 urges plunger 154 distally, thereby ensuring the rotation of cam latch 126 and anvil head assembly 112 to the non-tilted operative position. With reference briefly to FIGS. 9 and 14, as head assembly 112 is urged to the non-tilted position (FIG. 14), teeth 116a formed on post 116 of head assembly 112 mesh with teeth 194 formed on sleeve body 190 of sleeve member 115 to cause the proximal advancement of sleeve body 190, in the direction indicated by arrow "A" (FIG. 9). In this manner, sleeve member 115 is positioned to receive an anastomosis donut (not shown) about sleeve body 190.

Referring briefly to FIG. 12, in the pre-fired operative position of head assembly 112, i.e. when head assembly 112 has been pivoted to the non-tilted operative position and before firing of surgical stapler device 10, fingers 138 formed on backup plate 120 engage protrusions 152b adjacent top surface 152a of center rod 152 to prevent head assembly 112 from pivoting about pivot member 162.

With reference back to FIG. 1, anvil assembly 110 is operably received on an anvil retainer 32 extending from shell assembly 31 formed on a distal end of surgical stapling device 10. Once anvil assembly 110 is received on surgical stapling device 10, surgical stapling device 10 operates in the manner discussed in the '060 Patent, the content of which was previously incorporated herein in its entirety. Note that alternatively, first suture "S₁" (FIG. 7) may be severed after the distal head portion 16 of the surgical stapling device 10 receives anvil assembly 110. After attachment, the rotation knob 22 is rotated to approximate anvil assembly 110 and distal head portion 16 to clamp tissue therebetween, and then firing trigger 20 is actuated to fire the staples (not shown) as disclosed in the '060 Patent. As seen in FIG. 2, when anvil head assembly 112 is in the non-tilted operative position, sleeve body 190 of sleeve member 115 is disposed adjacent to and between anvil head assembly 112 and shell assembly 31 (FIG. 1) to receive the anastomosis donut created during the anastomosis procedure.

The operation of anvil assembly 110 will now be described with reference to FIGS. 10-16. When anvil assembly 110 is in its pre-fired non-tilted, operative position (e.g. FIGS. 11 and 12), backup plate 120 is spaced from backwall 118a of housing 118 by retainer 127 and protrusions 152b of center rod 152 engage fingers 138 of backup plate 120 to prevent tilting of anvil head assembly 112 about pivot member 162. Finger 166 of plunger 154 is urged by spring 156 into engagement with body portion 126c of cam latch member 126 to urge cam latch member 126 in a clockwise direction (as viewed in FIG. 11), about pivot member 162 such that edge 126f of cam latch member 126 engages inner periphery 120b of backup member 120.

The firing of surgical stapling device 10 (FIG. 1) causes a knife blade (not shown) to engage cutting ring 122 to move cutting ring 122 and backup plate 120 into annular recess 136 of housing 118 of anvil head assembly 112. Arrows "W" in FIG. 13 indicate how cutting ring 122 and backup plate 120 move as a result of the firing of surgical stapling device 10. When such movement occurs, deformable tabs 127a of retainer 127 are deformed against backwall 118a of housing 118 and fingers 138 of backup member 120 move away from protrusions 152b of center rod 152. Further, inner periphery 120b of backup plate 120 moves past edge 126f of cam latch member 126 such that cam latch member 126 is urged to pivot about pivot member 162, in the direction indicated by arrow "B" (FIG. 15), by plunger 154 (spring biased distally) to a position in which body portion 126e of cam latch 126 is positioned in front of and engages backup plate 120. Engagement of plunger 154 with cam latch member 126 urges cam member 126 to further rotate clockwise which due to its configuration enables spring biased plunger 154 to move further distally so angled surface 167 of plunger 154 contacts a proximal surface of post 116 of anvil head assembly 112 to move the anvil head assembly 118 to the third, tilted position (FIG. 16). It is noted that anvil head assembly 112 will not immediately tilt to the second tilted position upon firing of surgical stapling device 10 (FIG. 1) because, upon firing, anvil head assembly 112 is in an approximated position, i.e., the anvil head assembly 112 is in close alignment with shell assembly 31 of stapling device 10, and, therefore, does not provide room for head assembly 112 to pivot. As such, the anvil head assembly 112 will only begin to tilt when anvil assembly 110 and shell assembly 31 of surgical stapling device 10 are being unapproximated and there is a sufficient gap between the anvil assembly 110 and the distal head portion 16 of the stapling device 10.

As anvil head assembly 112 pivots towards the second tilted position, finger 166 of plunger 154 maintains surface 126e of cam latch member 126 in contact with backup plate 120 to prevent backup plate 120 from sticking to the knife blade as the knife blade is retracted. It is noted that curved surface 126e of cam latch member is configured to eliminate any gap and ensure contact between surface 126e of cam latch member 126 and backup plate 120 to hold backup plate 120 in place during and after the knife blade is retracted such that the cutting ring and backup plate assembly stay in their correct position during continued tilting of anvil assembly 112.

With particular reference to FIG. 16, as anvil head assembly 112 pivots towards the second tilted position, teeth 116a formed on post 116 of anvil head assembly 112 continue to engage teeth 194 formed on sleeve body 190 of sleeve member 115 causing continued proximal advancement of sleeve body 190. As anvil head assembly 112 continues to pivot, teeth 116a formed on post 116 disengage teeth 194 formed on sleeve body 190. As teeth 116a and teeth 194 disengage, outwardly facing surface 116b of post 116 engages the distal end of bottom wall 190b of sleeve body 190, thereby further advancing sleeve body 190 distally as anvil head assembly 112 pivots. As discussed above, sleeve member 115 is configured such that an anastomosis donut (not shown) is formed about sleeve body 190 during firing of surgical stapling device 10. In this manner, as sleeve body 190 is advanced proximally by the movement of anvil head assembly 112, the anastomosis donut is also advanced proximally. As such, the anastomosis donut is moved away from anvil head assembly 112, thereby preventing the anastomosis donut from being pinched by anvil head assembly 112 and permitting a full range of movement of anvil head assembly 112 relative to center rod assembly 114.

Anvil assembly 110 is configured such that anvil head assembly 12 tilts to the second tilted position "β" degrees (FIG. 16) relative to center rod assembly 114. As can be appreciated, anvil head assembly 112 therefore pivots in a first direction from the first, tilted position to the non-tilted operative position for application of staples. After firing of the instrument, the anvil head pivots in the same clockwise direction to the second tilted position. In one embodiment, anvil head assembly 112 is tilted less than ninety degrees and preferably about seventy degrees (70°) to its second tilted position such that the total pivoting movement of the anvil from the retracted or first tilted position to the forward or second tilted position is about one-hundred and forty degrees (140°). It should however be noted that the tilting of anvil head assembly 112 to other degrees for the first and/or second tilted position is also contemplated.

It will be understood that various modifications may be made to the embodiments disclosed herein. For example, the presently disclosed sleeve assemblies may be modified for use on an anvil assembly having a head assembly capable of one hundred and twenty degrees (120°) of tilt, i.e., capable of being pivoted in a counter-clockwise direction prior to firing to facilitate positioning of the anvil assembly within a lumen. Those skilled in the art will envision other modifications within the scope and spirit of the claims appended hereto.

What is claimed is:

1. An anvil assembly comprising:
   an anvil center rod assembly;
   a head assembly pivotally secured to the anvil center rod assembly, the head assembly including a housing and a post extending from the housing, the post including a plurality of teeth; and
   a sleeve member including a sleeve body slidably disposed about the anvil center rod assembly, the sleeve body including a plurality of teeth directly engaged with the plurality of teeth of the post, wherein pivoting of the head assembly relative to the anvil center rod assembly causes corresponding longitudinal movement of the sleeve member relative to the anvil center rod assembly.

2. The anvil assembly of claim 1, wherein the head assembly is configured to pivot between a first tilted position, a non-tilted operated position, and a second tilted position.

3. The anvil assembly of claim 2, wherein pivoting of the anvil assembly from the non-tilted position to the second tilted position causes the sleeve body to move proximally relative to the anvil center rod assembly.

4. The anvil assembly of claim 2, wherein pivoting of the anvil assembly from the non-tilted position to the first tilted position causes the sleeve body to move distally relative to the anvil center rod assembly.

5. The anvil assembly of claim 1, wherein the head assembly is tilted seventy degrees (70°) relative to the anvil center rod assembly when the head assembly is in the first tilted position.

6. The anvil assembly of claim 1, wherein the head assembly is perpendicular to the anvil center rod when the head assembly is in the non-tilted operative position.

7. The anvil assembly of claim 1, wherein the head assembly is tilted seventy degrees (70°) relative to the anvil center rod assembly when the head assembly is in the second tilted position.

8. The anvil assembly of claim 1, wherein the head assembly moves through one hundred-forty degrees (140°) when the head assembly tilts from the first tilted position, through the non-tilted position, to the second tilted position.

9. The anvil assembly of claim 1, wherein pivoting of the head assembly relative to the anvil center rod assembly causes corresponding translation of the plurality of teeth of the sleeve body relative to the plurality of teeth of the post.

10. A surgical stapler comprising:
    a handle assembly;
    an elongated body portion extending distally from the handle assembly;
    a shell assembly secured to a distal end of the elongated body portion; and
    an anvil assembly selectively secured relative to the shell assembly, the anvil assembly including an anvil center rod assembly, a head assembly pivotally secured to the anvil center rod assembly, and a sleeve member slidably disposed about the anvil center rod assembly and directly engaged with the head assembly, the head assembly including a plurality of teeth in operative engagement with a plurality of teeth of the sleeve member, wherein pivoting of the head assembly relative to the anvil center rod assembly causes corresponding longitudinal movement of the sleeve member relative to the anvil center rod.

11. The surgical stapler of claim 10, wherein the sleeve member is disposed between the shell assembly and the head assembly during firing of the surgical stapler to receive an anastomosis donut.

12. The surgical stapler of claim 10, wherein the sleeve member is configured to move proximally as the head assembly is moved away from the shell assembly subsequent to firing of the surgical stapler.

13. The staple assembly of claim 10, wherein pivoting of the head assembly relative to the anvil center rod assembly causes corresponding translation of the plurality of teeth of the sleeve body relative to the plurality of teeth of the post.

* * * * *